(12) United States Patent
Schwanitz et al.

(10) Patent No.: US 6,348,205 B1
(45) Date of Patent: Feb. 19, 2002

(54) USE OF CARBONIC ACID FOR STABILIZING OR INCREASING THE EPIDERMAL CERAMIDE SYNTHESIS RATE

(75) Inventors: Hans-Joachim Schwanitz; Meike Bock, both of Osnabrück (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/581,114

(22) PCT Filed: Dec. 8, 1998

(86) PCT No.: PCT/EP98/07968

§ 371 Date: Aug. 21, 2000

§ 102(e) Date: Aug. 21, 2000

(87) PCT Pub. No.: WO99/29292

PCT Pub. Date: Jun. 17, 1999

(30) Foreign Application Priority Data

Dec. 9, 1997 (DE) .......................... 197 54 659

(51) Int. Cl.⁷ .............................. A61K 7/00; A61K 7/06
(52) U.S. Cl. ......................................... 424/401; 424/70.1
(58) Field of Search .............. 424/401, 70.1, 424/70.11

(56) References Cited

U.S. PATENT DOCUMENTS

| 5,110,603 A | | 5/1992 | Rau ........................... 424/466 |
| 5,472,698 A | * | 12/1995 | Rawlings ..................... 424/401 |
| 5,618,850 A | * | 4/1997 | Coury et al. .............. 514/772.2 |
| 5,667,769 A | * | 9/1997 | Kuckens et al. ........... 424/70.1 |

FOREIGN PATENT DOCUMENTS

EP 0 498 272 A 8/1992

* cited by examiner

Primary Examiner—Thurman K. Page
Assistant Examiner—Rachel M. Bennett
(74) Attorney, Agent, or Firm—Norris McLaughlin & Marcus

(57) ABSTRACT

The invention relates to the use of carbonic acid or $CO_2$ for producing a pharmaceutical or cosmetic preparation for topical application for stabilizing or increasing the epidermal ceramide synthesis rate. This improves the epidermal permeability barrier and reduces the transepidermal water loss. The preparation is additionally suitable for preventing or treating atopic dermatitis (neurodermatitis).

9 Claims, 2 Drawing Sheets n.s. = not significant *p < 0.05 **p < 0.01

USE OF CARBONIC ACID FOR STABILIZING OR INCREASING THE EPIDERMAL CERAMIDE SYNTHESIS RATE

This application is a 371 of PCT/EP 98/07968 filed Dec. 08, 1998.

The present invention relates to the use of carbonic acid for producing a pharmaceutical or cosmetic preparation for topical application for stabilizing or increasing the epidermal ceramide synthesis rate.

The outer boundary layer between a person and his surroundings is formed by the skin. One of the most important tasks of the skin is to form a barrier between external and internal environment. This barrier, which is of crucial importance for maintaining a constant internal environment, is referred to as a permeability barrier.

Numerous skin disorders are associated with a constitutional or acquired disturbance of the epidermal permeability barrier. A stabilization or the physiological building up of the permeability barrier is therefore an important aim of topical treatments and of crucial importance for example for people with a constitutionally sensitive skin (atopic diathesis of the skin), for people with dry skin as well as for preventing occupationally associated skin changes.

Although, in the final analysis, accurate assessment of the importance of all the individual epidermal lipids for maintaining the barrier function is not yet available, numerous investigations exist on the importance of the ceramides, one fraction of the epidermal lipids, for the barrier function. Thus, for example, G. Imokawa et al. (Arch. Dermatol. Res. (1989) 281: 45–51) were able to show that the water-binding function of the horny layer and the water permeability barrier function of the skin are primarily determined by the ceramide lipid fraction.

New findings of lipid research suggest that defects of epidermal lipid metabolism, and in particular a reduction of the amount of ceramides, lead to changes in the cohesion and desquamation of corneocytes. Impairments of the barrier function and conditions with disturbed hornification may be the consequence (O. Braun-Falco, G. Plewig, H. H. Wolff, Dermatologie und Venerologie, 4th edition, 1996, Springer Verlag, Berlin Heidelberg N.Y.).

Disturbances in the lipid pattern in atopic people (with a constitutionally increased skin sensitivity, atopic dermatitis, neurodermatitis, atopic eczema) have been detected in various investigations. Thus, J. Hollmann et al. (H+G (1996) 71: 115–120) were able to detect a reduction in the ceramide content of the horny layer in people with neurodermatitis.

A reduced activity of the enzyme sphingomyelinase was detected in the dry skin of the elderly (T. Yamamura et al., J. Dermatol. Sci. (1990) 1: 79–84). This enzyme is involved in ceramide synthesis, and a reduced activity leads to a deficiency of ceramides.

These investigations indicate that epidermal lipids and, in particular, epidermal ceramides are of central importance in the pathogenesis in particular of skin disorders associated with sebostasis (dry skin) and increased scale formation.

In the pharmaceutical and cosmetic industry various attempts have been made in the past, based on the increasing knowledge about the importance of epidermal ceramides for the barrier function of the skin, to incorporate physiological ceramides in cosmetics and thus introduce them into the skin. The production of such cosmetics is, however, not very profitable because of the technical complexity and the costs of the raw materials (ceramides). In addition, it is still doubtful whether there is in fact any incorporation into the epidermal barrier of ceramides applied topically.

It is known further that irradiation with UV-A and UV-B increases the epidermal ceramide synthesis rate. UV irradiation for skin changes associated with a compromised barrier function shows good therapeutic effects. However, this type of therapy often cannot be employed in the therapy of atopic eczema because a large proportion of atopic people are photosensitive. In addition, in view of the side effects, the risks of UV irradiation must be taken into account in the "cost-benefit" assessment of the use of this type of therapy.

A method for the therapeutic treatment of skin by $CO_2$-impregnated water is disclosed in DE 41 24 728. This is intended to treat intractable skin disorders and disturbances of blood flow. No increase in the epidermal ceramide synthesis rate is disclosed.

An increased utilization of oxygen in the skin through topical use of $CO_2$ is also disclosed by D. R. Hartmann et al. in Angiology 48 (4), 1997, pages 337–343.

An improved blood flow through topical use of $CO_2$, and the resulting use for treating skin ulcers and wounds is disclosed by T. Ito et al. in J. Invest. Dermatol. 93 (2), 1989, pages 259–262.

Thus the effect of $CO_2$ on peripheral blood flow disturbances and disorders attributable thereto, such as, for example, chronic ulcers and sores, is known.

Other skin disorders such as atopic dermatitis, and cumulative subtoxic or traumiterative eczemas, are, however, attributable not to blood flow disturbances but, inter alia, to disturbances of lipid synthesis, in particular of ceramide synthesis. There is thus a need for preparations which stabilize or increase epidermal ceramide synthesis.

It is thus an object of the present invention to provide a preparation which stabilizes or increases the epidermal ceramide synthesis rate.

It has now been found according to the invention that the application of carbonic acid or $CO_2$ stabilizes or increases the epidermal ceramide synthesis rate.

The invention thus relates to the use of carbonic acid and/or $CO_2$ for producing a pharmaceutical and/or cosmetic preparation for topical application for stabilizing or increasing the epidermal ceramide synthesis rate.

The stabilizing or increasing of the epidermal ceramide synthesis rate contributes to stabilizing or improving the integrity of the epidermal permeability barrier and thus to reducing the transepidermal water loss and to increasing the relative skin hydration. It is possible in this way, for example, to prevent or treat atopic xeroses, dry skin in the elderly and eczemas due to irritation and contact allergy of the skin.

It is thus possible in general to treat preventively or therapeutically, through a stabilization or increase of the epidermal ceramide synthesis rate, skin disorders due to moisture stress of the skin, such as, for example, a cumulative subtoxic or traumiterative eczema. These include occupational skin disorders, which are predominantly associated with an impaired permeability barrier. In addition, it is possible for a constitutionally increased skin sensitivity (atopic dermatitis, neurodermatitis, atopic eczema) to be treated preventively or therapeutically through a stabilization or increase of the epidermal ceramide synthesis rate.

For the purpose of the present invention, a preparation comprising carbonic acid or $CO_2$ as therapeutic active ingredient means any preparation which directly comprises carbonic acid or $CO_2$ or releases carbonic acid or $CO_2$ on the skin. Possible examples thereof are aqueous compositions which comprise $CO_2$ gas dissolved in-water, such as, in the simplest case, pure carbonated water. The preparation can, for example, also be in the form of a lotion, gel, foam, cream, washing or rinsing composition. Formulas for preparations containing carbonic acid are to be found, for example, in Derwent ref. 84-235086/78.

Likewise suitable are compositions which release carbonic acid only on contact with the skin or shortly before use. These may comprise, for example, compositions which are applied to the moist skin in order to release carbonic acid in a chemical reaction in contact with water. Examples to be mentioned of release of carbonic acid shortly before use are bath additives. These compositions which release carbonic acid only shortly before or on use of the medicament may comprise a carbonate salt (bicarbonate or hydrogen carbonate) such as sodium or potassium carbonate and an organic acid (for example fruit acids such as citric acid or tartaric acid) which release carbonic acid from the carbonate salt in the presence of water. These compositions preferably also comprise a wetting agent so that the reaction to release the carbonic acid starts as quickly as possible when the composition comes into contact with water.

The preparations according to the invention may comprise further conventional, pharmaceutically acceptable additives depending on the form and desired mode of use.

The effective concentration of carbonic acid in the preparation depends on the mode and duration of use and on the disorder to be treated and can easily be determined by the skilled worker.

The content of $CO_2$ gas in carbonated water may range, for example, from 350 mg/l to 1500 mg/l of water. The pH of the preparation achieved by the carbonic acid can be between 5 and 7, preferably at about 5.4.

The present invention thus makes available a dermatological therapeutic composition which may be optimal for a large number of patients. Optimal because carbonic acid occurs as physiological constituent of the body and, because of its chemical properties, cannot be overdosed. Unwanted side effects are therefore not to be expected.

Figure 1:
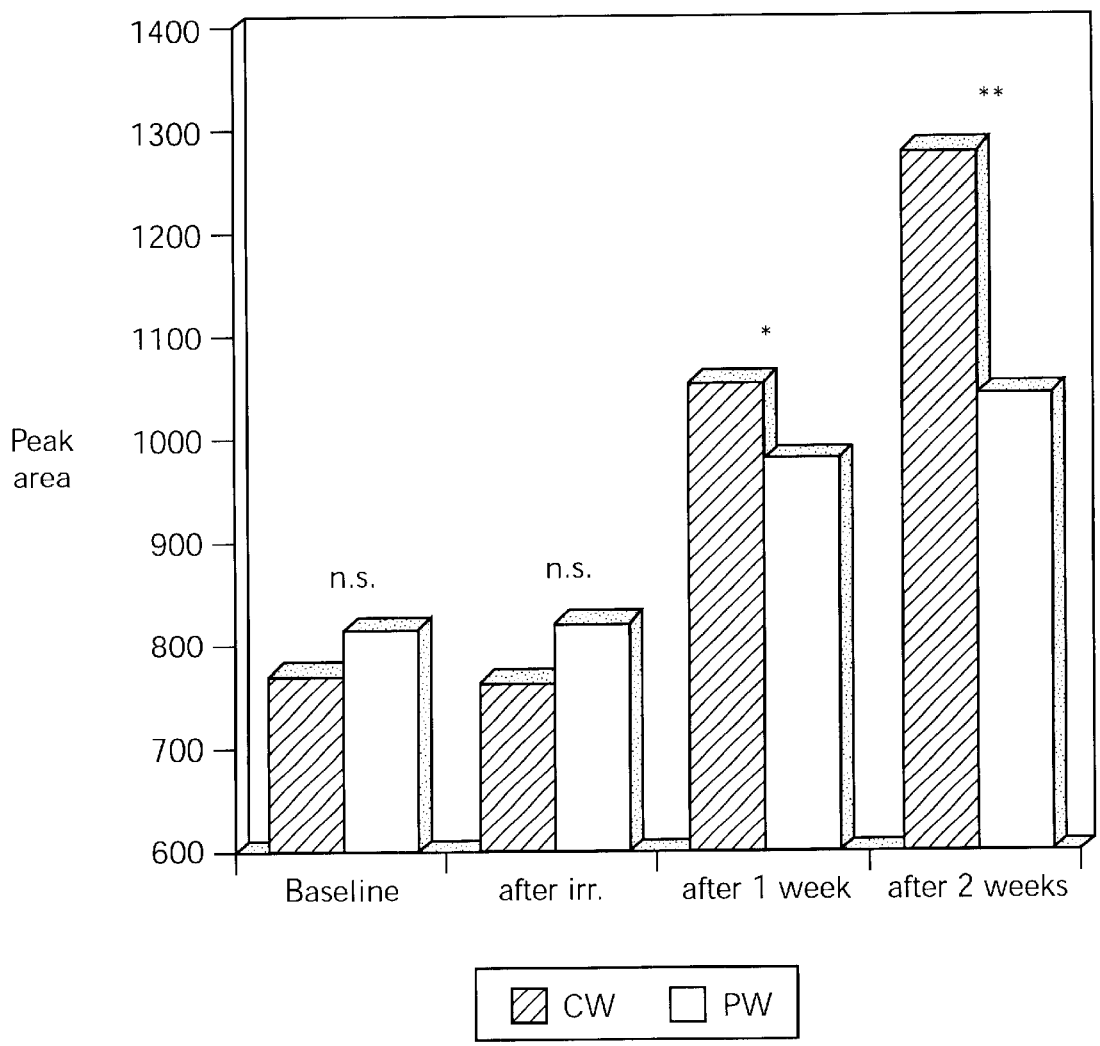
FIG. 1 shows the median peak areas for the ceramide fraction in the course of the investigation described in Example 1.

The following examples are intended to illustrate the present invention further.

EXAMPLE 1

This example illustrates the increase in the epidermal ceramide synthesis rate through the treatment with carbonic acid.

Methods

On the first investigation date, test plasters with 60 $\mu$l of 1% strength sodium lauryl sulfate (conventional synthetic surfactant frequently used in dermatological irritability research) were stuck onto in each case 3 test sites on the right and left forearm, and the epidermal lipids (baseline values before irritation) were obtained in vivo on the 4th test site on the right and left forearm. After 24 h, the test plasters were removed and all the previously irritated test sites were again irritated with sodium lauryl sulfate with occlusion for 24 h.

The intention of the cumulative irritation with sodium lauryl sulfate for 2×24 h on two consecutive days was initially to induce disturbance of the epidermal barrier, including damage to the epidermal lipid lamellae.

On the following investigation days (Monday to Friday), the forearms were rinsed each day with carbonic acid comparing with pure water for 1 min in each case. On the first investigation day after the irritation (Monday), the rinsing was preceded by in vivo delipidation in each case of one irritated test site on the forearm to be treated with carbonic acid and that to be treated with pure water. After use of carbonic acid or pure water for 5 and 10 days (Saturday) the delipidation took place in each case on one of the irritated test sites on the forearm treated with carbonic acid or pure water.

Pure water was used on the comparison side for reasons of standardization. The pure water, used as one-minute rinse, has no adverse effects on the permeability barrier, as has been shown both in our investigations and by other authors. Use of pure water on the comparison side thus makes it possible to state that the effects which are found are attributable exclusively to the carbonic acid.

The eluate of solvent and epidermal lipids obtained in vivo was initially evaporated under nitrogen, and the epidermal lipids were then frozen. In this way, the samples for chromatography were initially collected from all the subjects during the investigations.

For the investigations by thin-layer chromatography, the 8 samples from each subject were thawed and, using different concentrations of the standard mixture, developed and detected on a thin-layer plate.

Determination of the lipid pattern before irritation, immediately after irritation and after use for one week and two weeks of carbonic acid or pure water makes it possible to make detailed statements about the regeneration of the epidermal barrier and any effects of the use of carbonic acid on individual lipid fractions of the epidermal barrier lipids.

The parameter-free test method chosen for the statistical analysis was the WILCOXON paired differences test because it was necessary on the basis of the distribution density functions found for the baseline values to reject the hypothesis of a normal distribution.

The significance level in the event of rejection of the null hypothesis was fixed at $p<0.01$ (probability of error<1%).

Results

Comparability of the Test Areas Before Starting the Carbonic Acid Treatments

Compared with the baseline values for the total amount of lipids and for all detected lipid fractions, the WILCOXON paired differences test showed neither significant nor nearly significant differences between the baseline values for the forearm to be treated with pure water and that to be treated with carbonic acid.

After the cumulative irritation with sodium lauryl sulfate, the statistical analysis showed no significant or nearly significant differences between the test area to be treated with carbonic acid and that to be treated with pure water either for the delipidated total amount of lipids or for the individual detected lipid fractions.

Thus, comparability of the test areas on the forearm to be treated with pure water and that to be treated with carbonic acid is ensured in relation to the baseline values and the values measured after irritation for the total amount of lipids and for all detected lipid fractions.

Results for the Ceramide Lipid Fraction

FIG. 1 shows the median peak areas for the ceramide fraction at the various times of investigation. "CW" here means "carbonated water", and "PW" means "pure water".

No difference between the baseline values and the values after irritation for the ceramide fraction was detectable in the statistical analysis comparing the test area treated with carbonic acid and that treated with pure water.

However, the values for the ceramide fraction on the test area treated with carbonic acid were higher, nearly significantly so ($p<0.05$) after treatment for one week, and significantly so (p<0.01) after treatment for two weeks, than on the test area treated with pure water.

During the investigation there was found to be an increase in the peak areas found for the ceramide fraction both on the test area treated with carbonic acid and on that treated with pure water after treatment for one and two weeks. However, whereas the values for the ceramide fraction on the test area treated with pure water did not differ significantly after the treatments from the baseline values, the values detected on the test area treated with carbonic acid were significantly higher than the baseline values.

The epidermal barrier damage induced by sodium lauryl sulfate results in an increase in epidermal ceramide synthesis. It is possible to achieve by carbonic acid treatment a significant increase in the ceramide peak areas compared with the pure water treatment, which is to be regarded as a distinctly beneficial effect of the use of carbonic acid on epidermal ceramide synthesis after barrier damage.

EXAMPLE 2

This example shows the reduction in the transepidermal water loss (TEWL) and the increase in the relative skin hydration (RSH) and thus the improvement in the epidermal permeability barrier through treatment with carbonic acid.
Materials For the standardized washing, a normal commercially available shampoo which, according to the manufacturer, contains 1% active cleansing substances was diluted with distilled water until it contained 10% active cleansing substances in the solution ready for use.

Tap water was used for the part-affusions with pure water. The pH of the pure water was relatively constant at 8.2±0.1 throughout the test period.

The carbonated water employed was mechanically produced using an impregnation device in which tap water was supplemented with carbon dioxide under elevated pressure. The pH of the carbonated water (pH 5.4) was constant throughout the investigation.

All the part-affusions take place at a temperature of 37° C.
Methods

The test was carried out as unilateral test on 20 test subjects (13 women and 7 men between 23 and 28 years of age). The volunteer test subjects were not subjected to any selection conditions apart from right-handedness. For random distribution, one half of the participants was treated with carbonic acid on the right hand and the other half was treated on the left hand.

Over a period of 2 weeks, the back of one hand of the test subjects was rinsed with carbonic acid for 1 min once a day. The other was rinsed with pure water as control. At the same time, the backs of both hands were repeatedly irritated by a standardized washing with the shampoo solution twice a day.

The effect of carbonic acid or pure water on the dermatophysiological parameters of irritated skin was measured using noninvasive dermatophysiological investigation methods.

The transepidermal water loss (TEWL) as a measure of the permeability barrier function was measured using the evaporimetry method. An EP1 evaporimeter (Servomed & Co., Hasselby, Stockholm, Sweden) was used. The relative skin hydration (RSH) was measured using the capacitance measurement method. A CM 820 PC corneometer (Courage & Khazaka Electronic GmbH, Cologne, Germany) was used. The measurements have been reported as mean of 2 recordings (evaporimetry) or 3 recordings (corneometry).

All the tests took place in the partially air-conditioned dermatophysiology laboratory at Osnabrück University. Because there were only slight variations in the temperature (20°C.±1° C.) and humidity (48%±4%), it was possible to rule out varying correlations between temperature/humidity and the dermatophysiological parameters to be measured.

The investigations were preceded by a 30-minute acclimatization period in order to ensure that the subjects were acclimatized with the defined laboratory conditions. During the acclimatization period, a test area with a diameter of 1.5 cm was marked on the backs of the hands of the volunteers near to the middle metacarpophalangeal junction. After the acclimatization period, the baseline TEWL and RSH values were measured in all the test regions. The first washing took place immediately thereafter. Subsequently, the backs of the hands were rinsed with carbonic acid or pure water. The second measurements were carried out 30 min after the application because water causes, both on wetting and on rinsing off, a temporary but nevertheless marked increase in the hydration of the stratum corneum. Finally, the second washing took place in the same way as the first.
Statistical analysis The median and the 25/75% value were chosen as standard for the statistics. The WILCOXON paired differences test was used for the parameter-free statistics. It is regarded as a distribution-free analog of the t test for paired measurements and is to be understood as a symmetry test around the median of the differences (L. Sachs, Angewandte Statistik, 6th edition, Berlin, Springer-Verlag, 1984).

Figure 2:
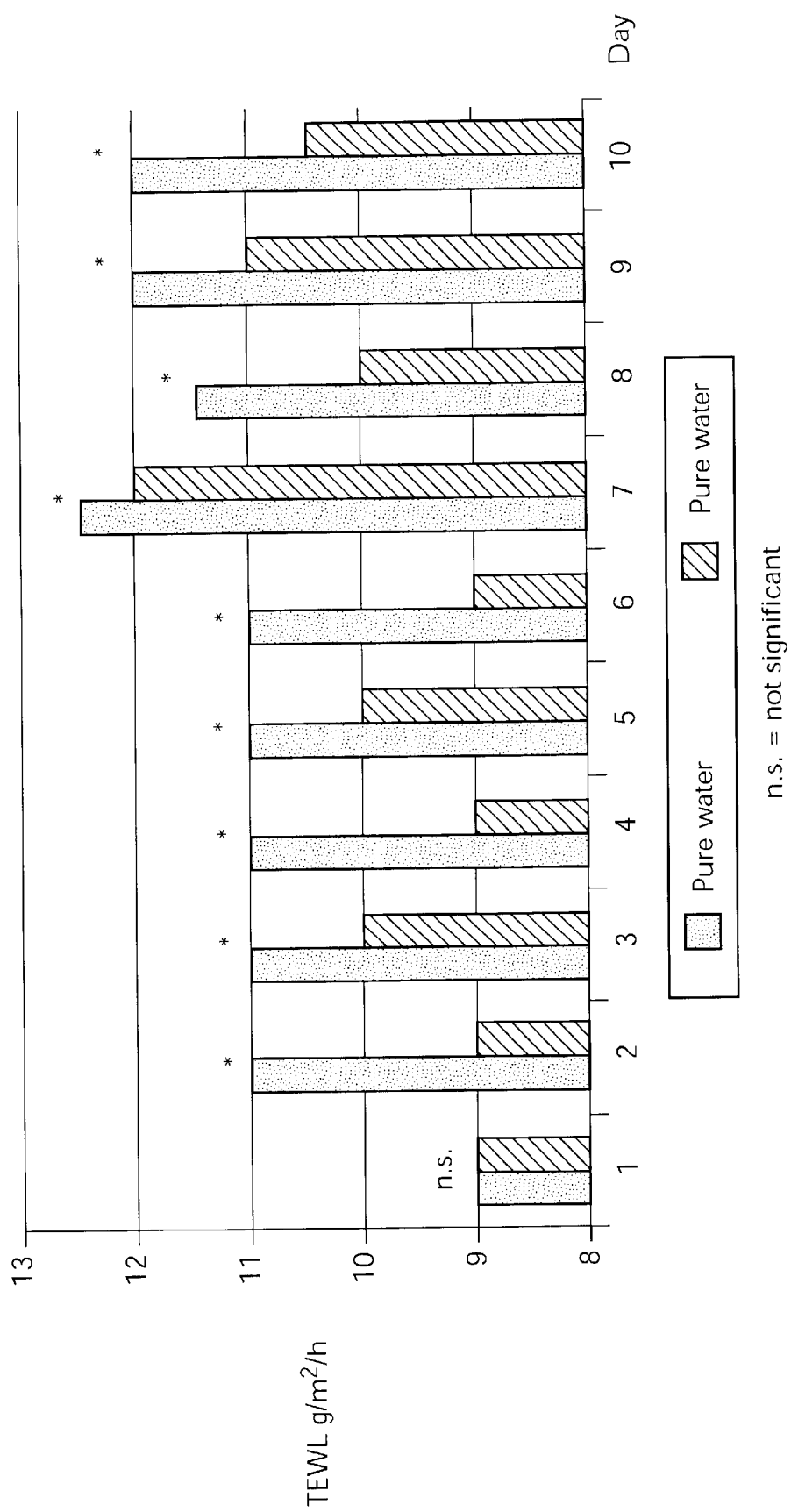
FIG. 2 shows the median transepidermal water losses (TEWL) in the course of the investigation described in Example 1.

Besides the ratio of the positive and negative differences, which makes statements about the connections between two parameters possible, the following level of significance was chosen: P<0.05.
Results The irritation caused by the repeated washings led to a significant increase in the TEWL values, both in combination with the pure water part-affusions and in combination with the carbonic acid part-affusions. However, comparison of the medians showed a smaller increase in the TEWL in the test areas treated with carbonic acid. The difference resulting from the smaller increase was marked in the WILCOXON paired differences test: on days 3, 6, 7 and 8 the TEWL values were significantly lower on test area treated with carbonic acid than on that treated with pure water. This beneficial effect of topically applied carbonic acid on the TEWL of irritated skin was even clearer on comparison of the values 30 min after use. With the exception of the first day, the TEWL of the test regions treated with carbonic acid 30 min after use was significantly lower than in the test regions treated with pure water. These results are reproduced in FIG. 2 which shows the TEWL medians in each case 30 min after use of carbonic acid or pure water during the investigation.

The baseline values of the RSH and of the RSH 30 min after use were higher (in some cases significantly higher) in the test zones treated with carbonic acid than in those treated with pure water.

This result shows that a controlled improvement in the permeability barrier, whose function correlates directly with the TEWL, can be achieved by topical application of carbonic acid. When it is remembered that a large number of skin disorders such as, for example, atopic xerosis, dry skin in the elderly and irritative and contact-allergic eczemas are thought to be connected with a disturbance of the permeability barrier, the significance of a controlled improvement in the permeability barrier becomes clear. Such an improvement is achieved by the present invention.

What is claimed is:

1. A method for stabilizing or increasing the rate of epidermal ceramide synthesis in the skin of humans, which comprises topically applying to said skin an amount effective therefor of carbonic acid, carbon dioxide or a combination thereof.

2. The method of claim 1, wherein said topical application stabilizes or improves the epidermal permeability barrier.

3. The method of claim 1, wherein said topical application reduces the transepidermal water loss.

4. The method of claim 1, wherein said topical application increases the relative skin hydration.

5. The method of claim 1, wherein said topical application prevents or treats skin disorders due to moisture stress.

6. The method of claim 1, wherein said topical application prevents or treats atopic dermatitis.

7. The method according to claim 1, which comprises topically applying to human skin an amount of carbonic acid effective for stabilizing or increasing the rate of epidermal ceramide synthesis in said human skin.

8. The method according to claim 1, which comprises topically applying to human skin an amount of carbon dioxide effective for stabilizing or increasing the rate of epidermal ceramide synthesis in said human skin.

9. The method according to claim 1, which comprises topically applying to human skin an amount of a combination of carbonic acid and carbon dioxide effective for stabilizing or increasing the rate of epidermal ceramide synthesis in said human skin.

* * * * *